US011596725B2

(12) United States Patent
Maierhofer (10) Patent No.: US 11,596,725 B2
(45) Date of Patent: Mar. 7, 2023

(54) DEVICE FOR AN EXTRACORPOREAL BLOOD TREATMENT, AND METHOD FOR DETERMINING A HEMODYNAMIC PARAMETER DURING AN EXTRACORPOREAL BLOOD TREATMENT

(71) Applicant: FRESENIUS MEDICAL CARE DEUTSCHLAND GMBH, Bad Homburg (DE)

(72) Inventor: Andreas Maierhofer, Schweinfurt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 612 days.

(21) Appl. No.: 16/619,477

(22) PCT Filed: Jun. 7, 2018

(86) PCT No.: PCT/EP2018/065066
§ 371 (c)(1),
(2) Date: Dec. 5, 2019

(87) PCT Pub. No.: WO2018/224606
PCT Pub. Date: Dec. 13, 2018

(65) Prior Publication Data
US 2020/0188572 A1   Jun. 18, 2020

(30) Foreign Application Priority Data
Jun. 10, 2017 (DE) ...................... 10 2017 005 534.3

(51) Int. Cl.
*A61M 1/36* (2006.01)
(52) U.S. Cl.
CPC ........ *A61M 1/3658* (2014.02); *A61M 1/3607* (2014.02); *A61M 1/3655* (2013.01);
(Continued)

(58) Field of Classification Search
CPC .............. A61M 1/3658; A61M 1/3607; A61M 1/3655; A61M 1/3656; A61M 1/3659;
(Continued)

(56) References Cited

U.S. PATENT DOCUMENTS

| 5,830,365 | A | 11/1998 | Schneditz | |
| 6,776,770 | B1* | 8/2004 | Trerotola | A61M 25/00 604/6.11 |

(Continued)

FOREIGN PATENT DOCUMENTS

| CN | 103561793 A | 2/2014 |
| CN | 104349803 A | 2/2015 |

(Continued)

OTHER PUBLICATIONS

International Preliminary Report on Patentability issued in corresponding International Patent Application No. PCT/EP2018/065066 dated Dec. 10, 2019 (English translation) (8 pages).

(Continued)

*Primary Examiner* — John Kim
(74) *Attorney, Agent, or Firm* — Kilyk & Bowersox, P.L.L.C.

(57) ABSTRACT

The invention relates to a device for extracorporeal blood treatment, comprising a blood treatment unit 1 that comprises at least one compartment 4. The invention further relates to a method for determining a hemodynamic parameter during an extracorporeal blood treatment by means of an extracorporeal blood treatment device. In order to determine the hemodynamic parameter, the conveying direction of the blood pump 10 is reversed from a "normal" blood flow to a "reversed" blood flow. In practice, it has been found that reversing the conveying direction of the blood pump for a measurement for determining a hemodynamic parameter carries the risk of blood clots reaching the patient, (Continued)

despite the dialyser holding back blood clots. The blood treatment device comprises an input unit 23 for inputting a time interval which can be specified by the user, taking into account the patient-specific and system-specific factors. The control and evaluation unit 12 of the blood treatment device is configured such that the operation of the blood pump 10 in the operating mode involving a reversed blood flow is only enabled during the time interval input by means of the input unit, the start of the time interval being determined from the point at which the blood treatment starts.

20 Claims, 1 Drawing Sheet

(52) U.S. Cl.
CPC ........ *A61M 1/3656* (2014.02); *A61M 1/3659* (2014.02); *A61M 1/3661* (2014.02); *A61M 1/3663* (2013.01); *A61M 1/3672* (2013.01); *A61M 2205/3317* (2013.01); *A61M 2205/3368* (2013.01); *A61M 2205/505* (2013.01)

(58) Field of Classification Search
CPC .............. A61M 1/3661; A61M 1/3663; A61M 1/3672; A61M 2205/505; A61M 2205/3317; A61M 2205/3368
See application file for complete search history.

(56) References Cited

U.S. PATENT DOCUMENTS

| | | | |
|---|---|---|---|
| 9,415,151 | B2 | 8/2016 | Schlaeper et al. |
| 11,324,868 | B2* | 5/2022 | Maierhofer ......... A61M 1/3635 |
| 2006/0079827 | A1 | 4/2006 | Jensen et al. |
| 2014/0083917 | A1 | 3/2014 | Okabe et al. |
| 2015/0021244 | A1 | 1/2015 | Furuhashi et al. |
| 2015/0246169 | A1* | 9/2015 | Humes ................... A61K 31/00 |
| | | | 435/375 |
| 2015/0343129 | A1 | 12/2015 | Surace et al. |

FOREIGN PATENT DOCUMENTS

| | | |
|---|---|---|
| CN | 105107042 A | 12/2015 |
| DE | 19528907 C1 | 11/1996 |
| WO | 2018001996 A1 | 1/2018 |

OTHER PUBLICATIONS

International Search Report and Written Opinion issued in corresponding International Patent Application No. PCT/EP2018/065066(with English translation of International Search Report) dated Sep. 3, 2018 (16 pages).

* cited by examiner

DEVICE FOR AN EXTRACORPOREAL BLOOD TREATMENT, AND METHOD FOR DETERMINING A HEMODYNAMIC PARAMETER DURING AN EXTRACORPOREAL BLOOD TREATMENT

This application is a National Stage Application of PCT/EP2018/065066, filed Jun. 7, 2018, which claims priority to German Patent Application No. 10 2017 005 534.3, filed Jun. 10, 2017.

The invention relates to a device for extracorporeal blood treatment, comprising a blood treatment unit that comprises at least one compartment. The invention further relates to a method for determining a hemodynamic parameter during an extracorporeal blood treatment by means of an extracorporeal blood treatment device.

In methods of chronic blood purification therapy, such as hemodialysis, hemofiltration and hemodiafiltration, blood is passed through an extracorporeal blood circuit. In hemodialysis, the blood to be treated flows through the blood chamber of a dialyser that is divided into the blood chamber and a dialysate chamber by a semi-permeable membrane, while dialysate flows through the dialysate chamber of the dialyser in a dialysate system. The extracorporeal blood circuit comprises an arterial hose line, which leads to the blood chamber, and a venous hose line, which leads out of the blood chamber. Known blood treatment devices have a blood pump, which is generally arranged upstream of the blood chamber of the dialyser in order to ensure sufficient blood flow in the extracorporeal blood circuit.

An arteriovenous fistula is often applied surgically as an access to the patient's blood vessel system. The use of an implant is also possible. Perfusion through the fistula is important for the operability thereof. If the fistula flow falls below a critical value, there is a greater risk of fistula thrombosis which could involve the loss of the vascular access, and this is a significant complication in dialysis treatment (W. Bay et al.: Color Doppler flow predicts PTFE graft failure, J. Am. Soc. Nephrol. 5: 407 (1994)). The fistula flow being lower than the extracorporeal blood flow (QB) during the dialysis treatment leads to local fistula recirculation, a fraction of the blood that has been dialysed and fed back to the fistula by means of the venous blood line being fed back to the dialyser by means of the arterial blood line. Fistula recirculation (RA) significantly reduces dialysis efficiency (F. Gotch: "Models to predict recirculation and its effect on treatment time in single-needle dialysis" First Intl. Symposium on Single-Needle Dialysis, ed.: S. Rignoir. R. Vanholder and P. Invanovich, Cleveland, ISAO Press, 1984, page 305 et seq.).

Owing to the clinical relevance thereof, various methods for determining the blood flow in the vascular access (shunt flow) or for determining recirculation are known. Several methods are based on measuring a physical or chemical characteristic variable of the blood that is changed in the extracorporeal blood circuit. The physical or chemical characteristic variable may be the temperature, density or electrolyte composition of the blood, for example. The characteristic variable can be directly or indirectly changed in the extracorporeal blood circuit by changing a physical or chemical characteristic variable in the dialysate system.

A method for measuring shunt flow, referred to as thermodilution, is known from EDTNA-ERCA Journal 19, 6 (1993). In this known method, a brief drop in temperature is initiated in the dialysate system, is transferred to the venous segment of the extracorporeal blood circuit and, in the event of recirculation, subsequently leads to a detectable sudden change in temperature in the arterial segment of the extracorporeal blood circuit.

DE 195 28 907 C1 describes a method for determining cardiopulmonary recirculation, involving two successive measurements of the recirculation fraction that are taken before and after the blood flow in the extracorporeal circuit has been reversed. The blood flow can be reversed, in principle, by swapping the arterial and venous patient connections. Manually swapping the patient connections is, however, not without problems from a hygiene and safety point of view. Therefore, numerous devices for blood hose systems have been developed which cause the flow direction to be automatically reversed by the relevant hose line portions of the hose line system being interconnected in a crosswise manner. In this case, however, the flow direction is maintained in the part of the extracorporeal circuit that includes the dialyser. Therefore, the protective systems located in this part can be used both before and after the blood flow has been reversed.

A valve apparatus for automatically reversing the flow direction is known from WO 2014/074231 A1 for example.

As an alternative to the known valve apparatuses for automatically reversing the flow direction, DE 195 28 907 C1 proposes simply reversing the conveying direction of the blood pump in the extracorporeal blood circuit. However, in practice, this option has not been used as of yet because operating an extracorporeal blood treatment device comprising a dialyser through which blood flows in various directions has not been found to be without problems in terms of safety.

The object of the invention is to make it possible to measure a hemodynamic parameter without using the known valve apparatuses for automatically reversing the flow direction which cause the flow direction to be automatically reversed by the relevant hose line portions of the hose line system being interconnected in a crosswise manner.

This object is achieved by the features of the independent claims. The dependent claims relate to preferred embodiments of the invention.

In order to prevent blood clots from forming in the extracorporeal blood circuit, an anticoagulant substance, usually heparin, is often added, in the form of an initial bolus, to the patient's blood either continuously during the blood treatment or at the start of the blood treatment. This anticoagulant substance is usually added upstream of the dialyser. In addition to the systemic effect of the anticoagulant substance in the patient, another possible mechanism of action is the accumulation of this substance on the surfaces of the extracorporeal system, in particular on the lumen of the dialyser fibres.

The dialyser used in an extracorporeal blood treatment is an impassable barrier for clots owing to the diameter of the hollow fibres of less than 0.2 mm. Therefore, clots forming upstream of the dialyser cannot reach the region downstream of the dialyser and thus cannot reach the patient. However, blood clots located downstream of the dialyser may be infused. This is independent of the flow direction of the blood through the dialyser.

In known blood treatment devices, clots forming in the blood travelling from the dialyser to the patient are generally held back by means of a device which is intended for catching blood clots and is provided downstream of the dialyser in the venous blood line of the extracorporeal hose system, ahead of the venous cannula. This device is also referred to as a "blood clot catcher".

In practice, it has been found that reversing the conveying direction of the blood pump for a measurement for determining a hemodynamic parameter carries the risk of blood clots reaching the patient, despite the dialyser holding back blood clots forming upstream of the dialyser. In practice, it has been found that blood clots accumulate at the inlet of the dialyser during operation at a "normal" blood flow. When the blood flow is reversed, these blood clots are flushed towards the patient.

It is irrelevant for the invention which hemodynamic parameters are determined on the basis of one or more measurements taken when the blood flow is reversed or how the hemodynamic parameters are determined. It is also irrelevant whether blood-side or dialysate-side variables are measured. Rather than the physical or chemical property of the blood in the blood line, a characteristic variable in the dialysate can also be measured that correlates with the physical or chemical characteristic variable in the blood line. In this respect, the invention relates to all methods in which a chemical or physical characteristic variable is measured before and after the flow direction has been reversed or only when the blood flow is reversed, in order to determine the hemodynamic parameter.

The invention relates, for example, to all methods in which, before and after the flow direction has been reversed, a chemical or physical characteristic variable in the blood in one segment of the extracorporeal blood circuit is changed, and the change in the chemical or physical characteristic variable in the blood in another segment of the extracorporeal blood circuit or in the dialysate is detected, which change can be attributed to the change in the chemical of physical characteristic variable in the first segment.

In order to determine the hemodynamic parameter, it is possible to measure the course of the observable change with respect to time in the physical or chemical characteristic variable in the blood-side or dialysate-side line system. A specific application is that of determining recirculation using known methods which require the flow direction to be reversed. In this case, the hemodynamic parameter can be the recirculation in the fistula or the shunt flow.

The blood treatment unit may be any unit for carrying out hemodialysis, hemofiltration, hemodiafiltration, apheresis or the like. In the case of hemodialysis, hemofiltration and hemodiafiltration, the blood treatment unit (dialyser) comprises a first and a second compartment that are separated from one another by a semi-permeable membrane. By contrast, when the blood treatment does not involve diffusive or convective substance exchange, for example adsorption on functionalised surfaces, a second compartment is not required.

The device according to the invention for extracorporeal blood treatment comprises:

a blood treatment unit comprising at least one compartment, a first blood line which is connected to a connection of the compartment and comprises a first patient connection, a second blood line which is connected to a connection of the compartment and comprises a second patient connection, a blood pump for conveying blood, an apparatus for measuring a physical or chemical characteristic variable, and a control and evaluation unit which is connected to the blood pump and to the apparatus for measuring a physical or chemical characteristic variable.

A first embodiment of the blood treatment device and of the method according to the invention proposes determining the hemodynamic parameter on the basis of a measurement involving two measurement cycles. In this embodiment, the control and evaluation unit is configured such that, for one measurement cycle of two measurement cycles, the blood pump is operated in an operating mode involving a reversed blood flow, such that blood flows from the second patient connection to the blood treatment unit and from the blood treatment unit to the first patient connection, and, for the other measurement cycle of the two measurement cycles, the blood pump is operated in an operating mode involving a normal blood flow, such that blood flows from the first patient connection to the blood treatment unit and from the blood treatment unit to the second patient connection, the hemodynamic parameter being determined from the measured physical or chemical characteristic variable in the measurement cycle when the blood flow is normal and when the blood flow is reversed. The measurement cycle involving a normal blood flow can precede the measurement cycle involving a reversed blood flow, or the measurement cycle involving a reversed blood flow can precede the measurement cycle involving a normal blood flow.

An alternative embodiment of the blood treatment device and of the method according to the invention proposes determining the hemodynamic parameter on the basis of just one measurement in an operating mode involving a reversed blood flow, such that blood flows from the second patient connection to the blood treatment unit and from the blood treatment unit to the first patient connection, the hemodynamic parameter being determined from the measured physical or chemical characteristic variable in the measurement cycle when the blood flow is reversed.

However, what is common to the two measurement methods is the fact that the blood pump is operated in an operating mode involving a reversed blood flow, which, in principle, runs the risk of clot formation because, in the known blood treatment devices, a device for collecting clots is generally not provided in the blood line leading from the dialyser to the second patient connection.

The device according to the invention and the method according to the invention involve reversing the blood flow in order to determine the hemodynamic parameter, despite there being, in principle, the risk of blood clot formation. At the start of the blood treatment, the extracorporeal blood circuit is free of blood clots. In practice, it has been found that blood clots first appear at a relatively late stage in the blood treatment. The period of time during which blood clots have not yet formed is dependent on various patient-specific and system-specific factors. These factors include the patient's general disposition to blood clotting, the type and amount of anticoagulant substances (anticoagulants) used, the surface properties of the parts with which the blood comes into contact in the extracorporeal blood circuit, and the intensity of the contact between the air and the blood in the extracorporeal blood circuit.

The extracorporeal blood treatment device according to the invention comprises an input unit for inputting a time interval which can be specified by the user, taking into account the patient-specific and system-specific factors. The control and evaluation unit of the extracorporeal blood treatment device is configured such that the operation of the blood pump in the operating mode involving a reversed blood flow is only enabled during the time interval input by means of the input unit.

The start of the time interval is preferably determined from the point at which the blood treatment starts. The start of the blood treatment can be defined as the point at which blood starts to flow in the extracorporeal blood circuit, for example when the blood pump is put into operation and the venous and arterial tube clamps are opened. The blood treatment can be preceded by a cleaning and/or test phase for preparing the blood treatment device for the blood treatment. In this phase, the extracorporeal blood circuit may be rinsed with a rinsing fluid, for example.

The control and evaluation unit is configured such that with the generation of a start signal for the blood treatment the start of the time interval is determined. For example, the control and evaluation unit may be configured such that the start signal is generated with the start of the blood pump and/or the opening of the venous and arterial tube clamps. At that time a timing element may begin to run, which enables the operation of the blood pump in the operating mode involving a reversed blood flow only within the input time interval. This timing element may be part of the control and evaluation unit.

After the time interval has elapsed, the blood pump can no longer be operated at a reversed blood flow, and therefore the patient is not at risk. It is therefore ruled out that a hemodynamic parameter be determined at a later point in the blood treatment, at which there is a risk of clot formation. The hemodynamic parameter to be determined may be, for example, recirculation or shunt flow.

One embodiment provides that the control and evaluation unit is configured such that, at the start of the blood treatment, the blood pump is operated in an operating mode involving a reversed blood flow, the hemodynamic parameter being determined from the measured physical or chemical characteristic variable in the measurement cycle when the blood flow is reversed. The blood treatment is therefore started at a reversed blood flow. Another embodiment provides that the blood flow is reversed only after an initial phase of the blood treatment has been carried out in which the blood pump is operated at a normal blood flow. In this phase, an initial bolus of an anticoagulant substance, for example heparin, can be added to the blood. As a result, the blood treatment involving the reversed blood flow can only start once the anticoagulant substance has been administered.

In order to add an anticoagulant substance to the blood, the device for extracorporeal blood treatment can comprise a metering apparatus, the control and evaluation unit being configured such that the metering apparatus is operated in the initial phase of the blood treatment in order for an anticoagulant substance to be added. In the initial phase of the blood treatment, the blood pump is preferably operated in an operating mode involving a normal blood flow. However, it is also possible for the anticoagulant substance to be continuously added during the blood treatment by means of the metering apparatus. In this case, the blood treatment can be started immediately at a reversed blood flow.

The time required for measuring shunt flow is highly dependent on the measurement method used. In known methods for determining a hemodynamic parameter, the measuring time can be relatively short if the physical or chemical characteristic variable is changed by adding a bolus of a particular substance directly to the extracorporeal blood circuit, for example. In this case, in order to accurately determine the shunt flow on the basis of a measurement taken at a reversed blood flow, it is not necessary to take an additional measurement at a normal blood flow, since the cardiopulmonary portion of the recirculation can be disregarded within the relatively short measuring time. In practice, it can take less than 20 to 30 seconds to measure the shunt flow. Methods for determining shunt flow that require a relatively long measuring time are however also known. This is the case for example in the methods known as thermodilution (EDTNA-ERCA Journal 19, 6 (1993)). In practice, it can take between 6 and 10 minutes to measure the shunt flow in these methods. However, in this case the shunt flow can be at least estimated after a single measurement has been taken at a reversed blood flow.

In an alternative embodiment, the control and evaluation unit is configured such that, at the start of the blood treatment or after an initial phase of the blood treatment has been carried out in which the blood pump is operated at a normal blood flow, the blood pump is operated, for a first measurement cycle, in an operating mode involving a reversed blood flow, and the blood pump is operated, for a second measurement cycle, in an operating mode involving a normal blood flow, the hemodynamic parameter being determined from the measured physical or chemical characteristic variable in the measurement cycle when the blood flow is normal and when the blood flow is reversed.

The alternative embodiment makes it possible to precisely determine the shunt flow using known methods, taking into account the cardiopulmonary recirculation.

The control and evaluation unit can be configured such that a control signal is generated at the end of the time interval if the blood pump is operated or intended to be operated in the operating mode involving a reversed blood flow. This control signal can be a signal that intervenes in the control such that it interrupts the blood flow in the reversed flow direction or prevents the flow direction from being reversed. The control signal can also actuate an alarm unit, which triggers an alarm. The lapse of the time interval can also be displayed on a display unit.

The control and evaluation unit can comprise a memory, the control and evaluation unit being configured such that the time interval from the input unit is read into the memory.

The input unit may comprise a keypad and/or a touch-sensitive screen and/or a device for reading a data medium, on which different values can be stored for several patients, which values can be selected by the user using the keypad or the touch-sensitive screen. The input unit can also be a component of a data processing unit which can be connected to the control and arithmetic unit via a network.

For operation at a normal blood flow, the device for extracorporeal blood treatment preferably comprises a device for collecting blood clots in the second blood line, and therefore blood clots forming downstream of the dialyser cannot reach the patient. When the blood flow is normal, the blood clots forming upstream of the dialyser are held back in the dialyser owing to the small lumen of the hollow fibres.

In the following, the invention is explained in greater detail with reference to the single FIGURE, which is a very simplified schematic view of a device for extracorporeal blood treatment.

Figure 1:
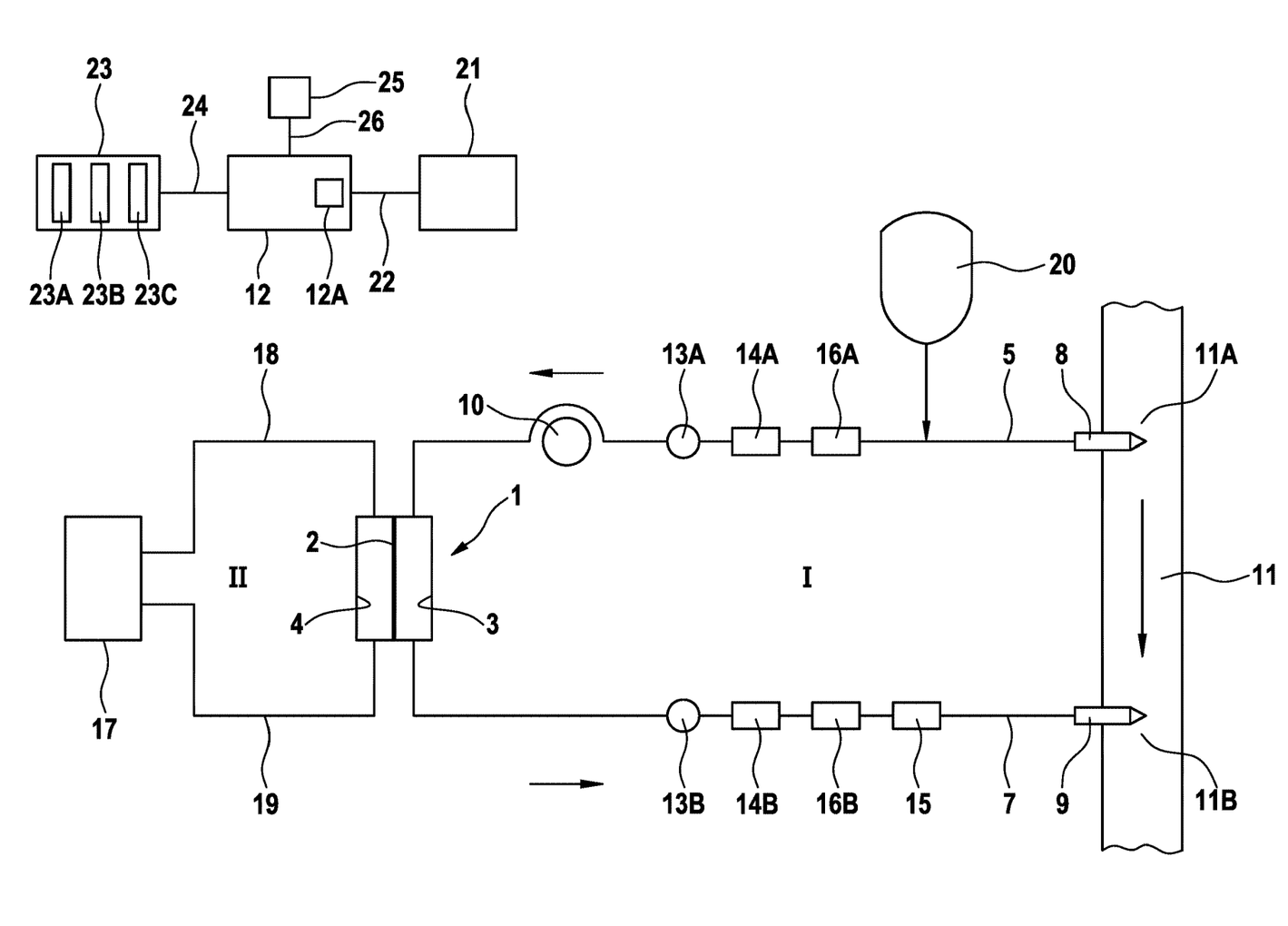

The FIGURE is a greatly simplified schematic view of the components of the blood treatment device that are essential to the invention, which blood treatment device is a hemodialysis device in the present embodiment. The blood treatment device comprises a blood treatment unit 1 which may be a dialyser that is divided into a first compartment 3 (blood chamber) and a second compartment 4 (dialysate chamber) by a semi-permeable membrane 2. The extracorporeal blood circuit I comprises a first blood line 5, which is connected to a first connection of the first compartment 3, the first compartment 3 and a second blood line 7, which is connected to a second connection of the first compartment 3. The first and second blood lines 5, 7 are hose lines of a blood hose system intended for single use (disposable). A first patient connection 8 (puncture cannula) is located at the end of the first blood line 5, and a second patient connection 9 (puncture cannula) is located at the end of the second blood line 7. The blood is conveyed by means of a blood pump 10, which is provided in the first blood line 5.

In order to carry out the blood treatment, the first puncture cannula 8 is connected to an upstream part 11A of the vascular access 11, whereas the second puncture cannula 9 is connected to a downstream part 11B of the vascular access 11, such that the patient's blood flows through the first blood line 5, the first compartment 3 of the blood treatment unit 3 and the second blood line 7. This case is referred to as "normal" blood flow. In this case, the blood pump 10 conveys blood in the "normal" conveying direction. The upstream part 11A of the vascular access 11 is thus the arterial part of the fistula, the first blood line 5 is the arterial blood line, the second blood line 7 is the venous blood line, and the downstream part 11B of the fistula is the venous part of the fistula.

In order to determine the hemodynamic parameter, in particular the shunt flow, it is required that the flow direction be reversed such that the blood flows from the downstream part 11B of the vascular access 11, through the second blood line 7, the first compartment 3 of the blood treatment unit 1 and the first blood line 5, to the upstream part 11A of the vascular access 11. This case is referred to as "reversed" blood flow. In this case, the blood pump 10 conveys blood in the "reversed" conveying direction.

The blood treatment device has a central control and evaluation unit 12 for controlling all the components of the device. The control and evaluation unit 12 can have, for example, a general processor, a digital signal processor (DSP) for continuously processing digital signals, a microprocessor, an application-specific integrated circuit (ASIC), an integrated circuit consisting of logic elements (FPGA) or other integrated circuits (IC) or hardware components, in order to perform the individual method steps for controlling the blood treatment device. A data processing program (software) can run on the hardware components in order to carry out the method steps. A plurality or combination of the various components is also possible.

The control and evaluation unit 12 is configured such that the individual components of the blood treatment device are actuated in order to carry out the blood treatment, and the measurements are taken in order to determine a hemodynamic parameter of the blood treatment.

In the first blood line 5 between the blood pump 10 and the first patient connection 8, the blood treatment device comprises a first pressure sensor 13A for measuring pressure and, in the second blood line 7 between the first compartment 3 and the second patient connection 9, said device comprises a second pressure sensor 13B for measuring pressure.

The measurements for determining a hemodynamic parameter of the blood treatment can be taken in the extracorporeal blood circuit I. A first measurement apparatus 14A is provided in the first blood line 5 in order to measure a physical or chemical property of the blood, and a second measurement apparatus 14B is provided in the second blood line 7 in order to measure a physical or chemical property of the blood. The pressure sensors 13A, 13B and the apparatuses 14A, 14B for measuring a physical or chemical property of the blood are connected to the control and evaluation unit 12 via data lines (not shown). A device 15 for catching blood clots is provided in the second blood line 7, between the second apparatus 14B for measuring a physical or chemical property and the second patient connection 9. However, the blood clot catcher 15 can also be provided in a different portion of the second blood line 7.

The blood treatment device can comprise additional monitoring and safety apparatuses 16A, 16B (only shown in outline) which can operate in both the "normal" and "reversed" flow direction. These monitoring and safety apparatuses 16A, 16B include an air separation chamber, an air detector and a valve in the first blood line and the second blood line. The air separation chambers can have inlet and outlet lines which are arranged below the liquid level. Ultrasonic sensors can be used to detect air.

Furthermore, the blood treatment device comprises a metering apparatus 20 (only shown schematically) for adding an anticoagulant substance (anticoagulant), for example heparin, to the patient's blood. When the blood flow is normal, the anticoagulant substance is added in the first blood line 5, upstream of the blood treatment unit 1. The metering apparatus 20 may be a syringe pump, for example, which is connected to the first blood line via a hose line. A syringe filled with heparin solution can be inserted into the syringe pump. The metering apparatus 20 can however also comprise a bag filled with heparin solution.

The dialysate system II comprises an apparatus 17 for preparing dialysate at a specified temperature. The fresh dialysate flows into the second compartment 4 via a dialysate feed line 18, and the used dialysate flows from the second compartment 4 of the blood treatment unit 1 to the apparatus 17 for preparing dialysate via a dialysate removal line 19. The apparatus 17 for preparing dialysate is connected to the control and evaluation unit 12 via a data line (not shown) such that the control and evaluation unit 12 can control the temperature and composition of the dialysate.

The measurements for determining a hemodynamic parameter of the blood treatment can also be taken in the dialysate system II, instead of in the extracorporeal blood circuit I. These methods can be found in the prior art. For example, the fistula flow can thus be determined by measuring the clearance when the blood flow is normal and when the blood flow is reversed.

In the case of hemofiltration, there is no need for an apparatus for preparing dialysate or a dialysate feed line leading to the second compartment of the blood treatment unit. Ultrafiltrate can be removed from the second compartment of the blood treatment unit via the dialysate removal line. For a blood treatment in which there is no diffusive or convective exchange, there is no need for a second compartment or a dialysate feed or removal line either. The only important factor for the invention is that the flow has to be reversed in order to determine the hemodynamic parameter. It is not important for the invention whether a physical or chemical characteristic variable is changed in order to determine the hemodynamic parameter in the blood. The physical or chemical characteristic variable can be measured on the blood side or on the dialysate side.

In the present embodiment, the apparatus 17 for preparing dialysate also acts as an apparatus for changing a physical or chemical property of the blood. For this purpose, the apparatus 17 for preparing dialysate temporarily changes the temperature or composition of the dialysate in the dialysate system II, and this results in a change in a physical or chemical property in the extracorporeal blood circuit I. The change in the physical or chemical property in the blood, for example the temperature of the blood (temperature bolus), is measured by means of the first or second measurement apparatus 14A, 14B in the first and second blood lines 5, 7, respectively. Alternatively, the change in the physical or chemical property of the blood can also occur as a result of external elements such as Peltier elements attached to the blood hose system or as a result of the infusion of a physiological solution via an addition site in the first blood line or the second blood line.

The running direction and conveyance rate of the blood pump 10 can be controlled by means of the control and evaluation unit 12. For this purpose, the pressure values from the pressure sensors 13A, 13B can be used in order to determine and correct, in a known manner, the effective blood flow from the rotational speed of the pump and the negative pressure on the relevant intake side.

The course with respect to time of the physical or chemical property of the removed blood and the returned blood is measured and transmitted to the control and evaluation unit 12 by means of the measurement apparatuses 14A, 14B provided on the blood hose system. The measurement apparatuses 14A, 14B may be, for example, temperature sensors, optical or spectroscopic sensors or density sensors, for example ultrasonic sensors. Conductivity measurement cells can also be used in order to determine variables that correlate with the relevant physical or chemical properties of the blood. Instead of the blood-side physical or chemical characteristic variables, dialysate-side physical or chemical characteristic variables can also be measured that correlate with the blood-side physical or chemical characteristic variables. For this purpose, measured value recorders for measuring the characteristic variables can be provided in the dialysate system II, for example in one or both of the dialysate lines 18 and 19.

In the present embodiment, the flow in the vascular access (shunt flow) is determined as the hemodynamic parameter. Shunt flow can be determined by means of the method described in DE 195 28 907 A1. The theoretical principles of the method are described in the article *ASAIO journal* 1998, Measurement of Access Flow During Hemodialysis Using the Constant Infusion Approach, Daniel Schneditz, Zuoheng Fan, Allen Kaufmann, and Nathan W. Levin, page 74 et seq.

A first embodiment is described in the following. The sequence for measuring the shunt flow is controlled by the control and evaluation unit 12. Firstly, the blood pump 10 is operated in the "normal" conveying direction. In this initial phase, when the blood pump 10 is running, the control and evaluation unit 12 can activate the metering apparatus 20 such that an anticoagulant substance is added to the patient's blood, which anticoagulant substance can also accumulate on the surfaces of the extracorporeal system, in particular on the lumen of the dialyser fibres. However, an initial phase of this type is not compulsory. The anticoagulant can also be added continuously. It is not crucial to the method that anticoagulants be added. The patient may have even received sufficient anticoagulant treatment prior to dialysis, e.g. by using Marcumar.

After the initial phase has been carried out, the control and evaluation unit 12 controls the blood pump such that the blood flow is reversed. The temperature or composition of the dialysate is temporarily changed when the blood flow is reversed. The temperature bolus or sudden change in conductivity is transferred to the extracorporeal blood circuit I as a result of heat being exchanged at the dialyser. The measurement apparatuses 14A, 14B in the first and second blood lines 5, 7, respectively, detect the changes in the physical or chemical characteristic variable in the first blood line and the second blood line. The measured values are stored in a memory unit 12A of the control and evaluation unit 12. Subsequently, the blood pump 10 is again operated in the normal conveying direction. The temperature or composition of the dialysate is temporarily changed when the blood flow is normal, and the temperature or composition of the dialysate is measured in the first blood line and the second blood line. Alternatively, the conductivity curve of the dialysate can be measured by means of conductivity cells (not shown), which are provided in the dialysate feed line 18 and the dialysate removal line 19. The measured values are again stored in the memory unit 12A of the control and evaluation unit 12. The control and evaluation unit 12 then calculates the flow in the vascular access on the basis of the measured values from the measurement apparatuses, using suitable sequence control and corresponding evaluation methods. The result can be displayed on a display unit 21, which is connected to the control and evaluation unit 12 via a data line 22, or output by means of another type of communication, for example via a network.

Potential error messages or instructions can also be transmitted to the user on the display unit 21. Instead of a display unit, an alarm unit can also be provided, on which an acoustic, visual or tactile alarm is emitted, for example when the filter is blocked.

The evaluation method for calculating the shunt flow from the measured values is described in DE 195 28 907 A1, to which reference is hereby explicitly made.

When the flow direction is being reversed, the control and evaluation unit 12 ensures that the protective apparatuses 16A, 16B provided for dialysis treatments are adapted to the reversal of the blood flow direction. This includes, in particular, arterial and venous pressure monitoring, the meaning of which is switched when the flow is reversed. Whilst there is negative pressure on the intake side ("arterial") of the blood pump, the pressure on the return side ("venous") is positive. At the same time, the venous pressure is used to detect potential needle disconnections. The control and evaluation unit 12 is therefore configured such that the specified arterial and venous pressure threshold values are switched when the flow is reversed. Using algorithms for detecting a needle disconnection, which are based on a dynamic signal analysis and/or which monitor whether the pressure on the return side has fallen below a lower pressure threshold in absolute terms, the measured values from the arterial sensor are now evaluated in normal operation rather than the measured values from the venous sensor. In addition, after the flow has been reversed, air infusion is monitored on the side that is arterial in normal operation.

In the present embodiment, the measurement is initially taken when the blood flow is reversed. However, it is also possible for the measurement to be initially taken when the blood flow is normal. However, initially operating the blood treatment device at a reversed blood flow after the initial phase is advantageous in that the switch to the reversed blood flow is made during the blood treatment at as early a stage as possible, i.e. not when clots may have already formed in the case of a previous normal blood flow.

The blood treatment device comprises an input unit 23 which is connected to the control and evaluation unit 12 via a data line 24. The input unit 23 can for example comprise a keypad 23A and/or a touch-sensitive screen 23B and/or a device 23C for reading a data medium. Using the input unit 23, the user can input a time interval which the user can set taking into account various patient-specific or system-specific factors. The input time interval is stored in the memory 12A of the control and evaluation unit 12.

The control and evaluation unit 12 is configured such that the operation of the blood pump 10 in the operating mode involving a reversed blood flow is only enabled during the time interval input by means of the input unit 23. In the present embodiment, the start of the time interval is the point at which the initial phase of the blood treatment starts.

The control and evaluation unit 12 comprises a timing element that is started at the start of the initial phase of the blood treatment. Before the blood flow is reversed, the control and evaluation unit 12 checks whether the time interval specified by the user has elapsed. If this is the case, the control and evaluation unit 12 prevents the blood flow from being reversed, i.e. once the timing element has run out, it is not possible to determine the hemodynamic parameter on the basis of a measurement taken at a reversed blood flow.

The control and evaluation unit 12 can be configured such that a control signal is generated at the end of the time interval if the blood pump 10 is already being operated in the operating mode involving a reversed blood flow. This control signal can cause the operation of the blood pump to be interrupted, as a result of which the measurement is terminated. The control signal can also activate an alarm unit 25, which is connected to the control and evaluation unit 12 via a data line 26. The termination of the measurement can also be displayed on the display unit 21.

The control and evaluation unit 12 can also be configured such that the reversal of the blood flow can be unblocked by the user, for example by appropriate input by means of the input unit, if it is ensured that the blood clots have been disintegrated, for example by an anticoagulant being administered.

A relatively long time, possibly of between 8 and 10 minutes, is required in order to take the above-described measurement using the known method of thermodilution. The hemodynamic parameter, in particular the recirculation, can however also be obtained by known methods in which a physical or chemical characteristic variable is changed directly in the extracorporeal blood circuit, for example by infusion of a physiological solution at an addition site provided on the blood line. The measuring time is relatively short in this case.

In order to carry out the measurement, the control and evaluation unit 12 switches the blood pump 10 into the reversed blood flow at the start of the blood treatment or after an initial phase. After the blood flow has been reversed, a bolus of the physiological solution is added to the blood in the return direction, i.e. in the first blood line 8, and the change is measured in the removal direction, i.e. in the second blood line. Since the cardiopulmonary recirculation portion can be disregarded when the measuring time is relatively short, the shunt flow can even be sufficiently accurately determined according to the measurement taken at the reversed blood flow. In this case, it is no longer necessary to take a measurement when the blood flow is normal (Lopet et al, "Vascular access monitoring evaluated from automated recirculation measurement", EDTNA-ERCA JOURNAL 27, page 17 et seq.).

The invention claimed is:

1. A device for extracorporeal blood treatment, comprising:
   a blood treatment unit comprising at least one compartment, the at least one compartment comprising a first connection and a second connection;
   a first blood line connected to the first connection of the at least one compartment, the first blood line comprising a first patient connection;
   a second blood line connected to the second connection of the at least one compartment, the second blood line comprising a second patient connection;
   a blood pump;
   a measuring apparatus configured to measure a physical or chemical characteristic variable;
   an input unit configured to receive an input comprising a time interval; and
   a control and evaluation unit connected to the blood pump and to the measuring apparatus and configured, to carry out a first measurement cycle and a second measurement cycle, wherein either
   for the first measurement cycle the blood pump is operated in an operating mode comprising a reversed blood flow, such that blood flows from the second patient connection to the blood treatment unit and from the blood treatment unit to the first patient connection, for the second measurement cycle the blood pump is operated in an operating mode comprising a normal blood flow, such that blood flows from the first patient connection to the blood treatment unit and from the blood treatment unit to the second patient connection, and a hemodynamic parameter is determined from a measured physical or chemical characteristic variable in the two measurement cycles when the blood flow is normal and when the blood flow is reversed, or,
   for the first measurement cycle, the blood pump is operated in an operating mode comprising a reversed blood flow, such that blood flows from the second patient connection to the blood treatment unit and from the blood treatment unit to the first patient connection, and the hemodynamic parameter is determined from the measured physical or chemical characteristic variable in the first measurement cycle when the blood flow is reversed,
   and further wherein
   the control and evaluation unit is further configured such that the operation of the blood pump in the operating mode comprising the reversed blood flow is only enabled during the time interval received by the input unit.

2. The device for extracorporeal blood treatment according to claim 1, wherein the control and evaluation unit is further configured such that, at the start of the blood treatment or after an initial phase of the blood treatment has been carried out, in which the blood pump is operated at the normal blood flow, the blood pump is operated in the operating mode comprising the reversed blood flow, and the hemodynamic parameter is determined from the measured physical or chemical characteristic variable in the first measurement cycle when the blood flow is reversed.

3. The device for extracorporeal blood treatment according to claim 2, wherein the device for extracorporeal blood treatment further comprises a metering apparatus configured to add an anticoagulant substance to the blood, the control and evaluation unit is connected to the metering apparatus, and the control and evaluation unit is further configured to operate the metering apparatus during the initial phase of the blood treatment such that the anticoagulant substance is added during the initial phase.

4. The device for extracorporeal blood treatment according to claim 3, wherein, during the initial phase of the blood treatment, the blood pump is operated in the operating mode comprising the normal blood flow.

5. The device for extracorporeal blood treatment according to claim 1, wherein the control and evaluation unit is further configured such that, at the start of the blood treatment or after an initial phase of the blood treatment has been carried out, in which the blood pump is operated at the normal blood flow, the blood pump is operated, for a first measurement cycle, in the operating mode comprising the reversed blood flow, and then the blood pump is operated, for the second measurement cycle, in the operating mode comprising the normal blood flow, and then the hemodynamic parameter is determined from the measured physical or chemical characteristic variable in the two measurement cycles when the blood flow is normal and when the blood flow is reversed.

6. The device for extracorporeal blood treatment according to claim 1, wherein the control and evaluation unit is further configured such that a control signal is generated at an end of the time interval when the blood pump is operated in the operating mode comprising the reversed blood flow.

7. The device for extracorporeal blood treatment according to claim 1, wherein the control and evaluation unit further comprises a memory, and the control and evaluation unit is further configured such that the control and evaluation unit saves the time interval received by the input unit, into the memory.

8. The device for extracorporeal blood treatment according to claim 1, wherein the input unit comprises at least one of a keypad, a touch-sensitive screen, and a device for reading a data medium.

9. The device for extracorporeal blood treatment according to claim 1, further comprising a blood clot collecting device in the second blood line.

10. The device according to claim 1, wherein the hemodynamic parameter is shunt flow.

11. A method for determining a hemodynamic parameter during an extracorporeal blood treatment, comprising:
  providing an extracorporeal blood treatment device comprising
    a blood treatment unit comprising at least one compartment, the a least one compartment comprising a first connection and a second connection,
    a first blood line connected to the first connection of the at least one compartment and comprising a first patient connection,
    a second blood line connected to the second connection of the at least one compartment and comprising a second patient connection,
    a blood pump, and
    a measuring apparatus for measuring a physical or chemical characteristic variable; and, wherein either
  for a first measurement cycle of two measurement cycles, the blood pump is operated in an operating mode comprising a reversed blood flow, such that blood flows from the second patient connection to the blood treatment unit and from the blood treatment unit to the first patient connection, and, for a second measurement cycle of the two measurement cycles, operating the blood pump in an operating mode comprising a normal blood flow, such that blood flows from the first patient connection to the blood treatment unit and from the blood treatment unit to the second patient connection, and a hemodynamic parameter is determined from a measured physical or chemical characteristic variable in the two measurement cycles when the blood flow is normal and when the blood flow is reversed, or,
  for the first measurement cycle, the blood pump is operated in an operating mode comprising a reversed blood flow, such that blood flows from the second patient connection to the blood treatment unit and from the blood treatment unit to the first patient connection, and the hemodynamic parameter is determined from the measured physical or chemical characteristic variable in the first measurement cycle when the blood flow is reversed,
  and further wherein the operation of the blood pump in the operating mode comprising a reversed blood flow is only enabled during a specified time interval.

12. The method according to claim 11, wherein, at the start of the blood treatment or after an initial phase of the blood treatment has been carried out, in which the blood pump is operated at the normal blood flow, the blood pump is operated in the operating mode comprising the reversed blood flow, and
  the hemodynamic parameter is determined from the measured physical or chemical characteristic variable in the first measurement cycle when the blood flow is reversed.

13. The method according to claim 11, wherein, at the start of the blood treatment or after an initial phase of the blood treatment has been carried out, in which the blood pump is operated at the normal blood flow, the blood pump is operated, for the first measurement cycle, in the operating mode comprising the reversed blood flow, then the blood pump is operated, for the second measurement cycle, in an operating mode comprising the normal blood flow, and then the hemodynamic parameter is determined from the measured physical or chemical characteristic variable in the two measurement cycles when the blood flow is normal and when the blood flow is reversed.

14. The method according to claim 13, further comprising adding an anticoagulant substance during the initial phase of the blood treatment.

15. The method according to claim 11, further comprising collecting blood clots in the second blood line.

16. A device for extracorporeal blood treatment, comprising:
  a blood treatment unit comprising at least one compartment, the at least one compartment comprising a first connection and a second connection;
  a first blood line connected to the first connection of the at least one compartment, the first blood line comprising a first patient connection;
  a second blood line connected to the second connection of the at least one compartment, the second blood line comprising a second patient connection;
  a blood pump;
  a measuring apparatus configured to measure a physical or chemical characteristic variable;
  an input unit configured to receive an input comprising a time interval; and
  a control and evaluation unit connected to the blood pump and to the measuring apparatus and configured to carry out a measurement cycle, wherein
  for the measurement cycle, the blood pump is operated in an operating mode comprising a reversed blood flow, such that blood flows from the second patient connection to the blood treatment unit and from the blood treatment unit to the first patient connection, and a hemodynamic parameter is determined from a measured physical or chemical characteristic variable measured during the measurement cycle,
  and further wherein
  the control and evaluation unit is further configured such that the operation of the blood pump in the operating mode comprising the reversed blood flow is only enabled during the time interval received by the input unit.

17. The device for extracorporeal blood treatment according to claim 16, wherein the control and evaluation unit is further configured such that, at the start of the blood treatment or after an initial phase of the blood treatment has been carried out, in which the blood pump is operated at the normal blood flow, the blood pump is operated in the operating mode comprising the reversed blood flow, and the hemodynamic parameter is determined from the measured physical or chemical characteristic variable measured during the measurement cycle.

18. The device for extracorporeal blood treatment according to claim 17, wherein the device for extracorporeal blood treatment further comprises a metering apparatus configured to add an anticoagulant substance to the blood, the control and evaluation unit is connected to the metering apparatus, and the control and evaluation unit is further configured to operate the metering apparatus during the initial phase of the blood treatment such that the anticoagulant substance is added during the initial phase.

19. The device for extracorporeal blood treatment according to claim 16, wherein the control and evaluation unit is further configured such that a control signal is generated at an end of the time interval when the blood pump is operated in the operating mode comprising the reversed blood flow.

20. The device for extracorporeal blood treatment according to claim 16, wherein the control and evaluation unit further comprises a memory, and the control and evaluation unit is further configured such that the control and evaluation unit saves the time interval received by the input unit, into the memory.

* * * * *